United States Patent [19]

Sampson et al.

[11] 4,425,120

[45] Jan. 10, 1984

[54] SHIELDED HYPODERMIC SYRINGE

[76] Inventors: Norma A. Sampson, 1713 Victoria Dr., Fullerton, Calif. 92631; Earl W. Sampson, 1211 N. Council Ave., Ontario, Calif. 91764

[21] Appl. No.: 368,692

[22] Filed: Apr. 15, 1982

[51] Int. Cl.³ .............................................. A61M 5/00
[52] U.S. Cl. ................................... 604/198; 604/263
[58] Field of Search ............... 604/197, 198, 192, 187, 604/171, 263

[56] References Cited

U.S. PATENT DOCUMENTS

| | | | |
|---|---|---|---|
| 2,571,653 | 10/1951 | Bastien | 604/198 |
| 3,780,734 | 12/1973 | Wulff | 604/197 |
| 4,170,993 | 10/1979 | Alvarez | 604/263 |

*Primary Examiner*—John D. Yasko
*Attorney, Agent, or Firm*—Gordon L. Peterson

[57] ABSTRACT

A hypodermic syringe comprising a barrel, a needle coupled to the barrel and terminating in a point and a needle guard mounted on the barrel for movement between an extended position in which the guard shields the needle and a retracted position in which the guard does not shield the needle. The guard can be releasably locked in the retracted position and locked in the extended position. Locking of the guard is accomplished by a track on the internal surface of the guard and track-engaging members on the barrel.

13 Claims, 4 Drawing Figures

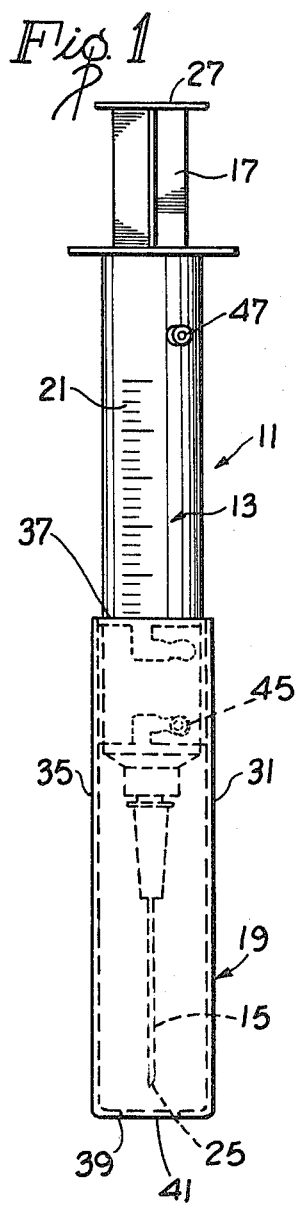
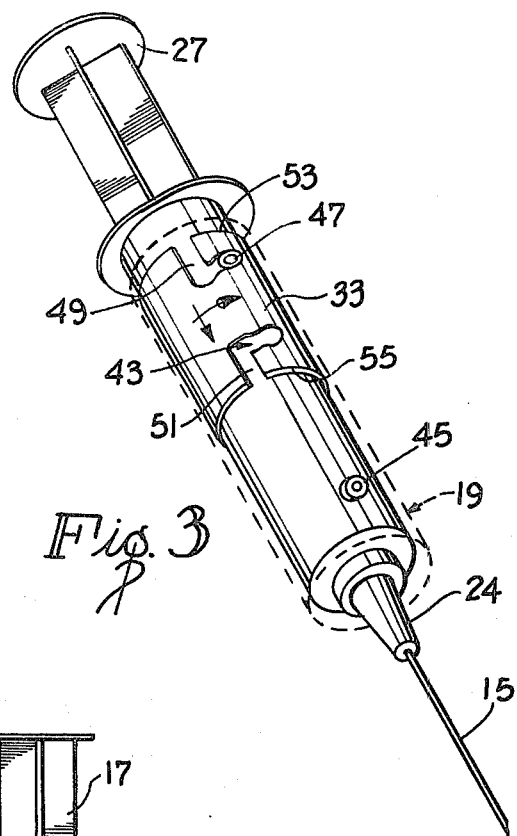
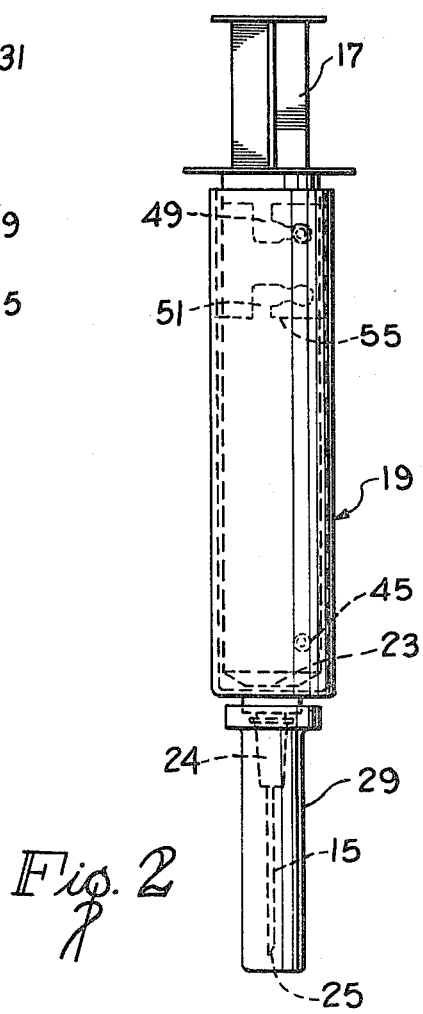
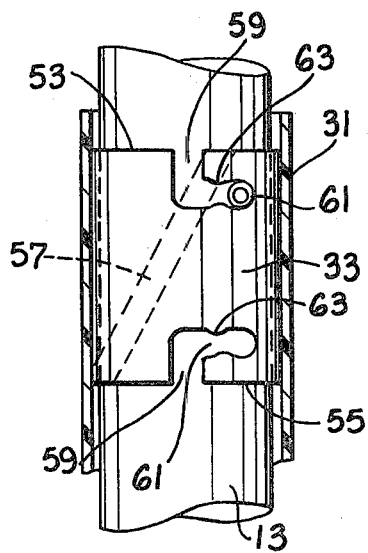

SHIELDED HYPODERMIC SYRINGE

BACKGROUND OF THE INVENTION

As is well known, a hypodermic syringe is used to inject substances into human and animal bodies. A typical hypodermic syringe comprises a barrel adapted to contain the substance to be injected, a hypodermic needle coupled to the barrel and means, such as a plunger, for forcing the substance from the barrel through the needle.

Hypodermic syringes are typically disposable and are discarded after use. One problem presented by the disposal of the syringes is in shielding the sharp end of the needle so that those handling it will not be stuck. This is particularly important because, following the injection, the needle may be contaminated and spread disease, such as hepatitis.

Typically, a hypodermic syringe is supplied with a tubular shield which is slipped over the needle from the pointed end and releasably retained on the syringe. One way to shield the needle following its use is to replace the tubular shield. Unfortunately, the passage into the shield is of small diameter and the shield must be inserted over the sharp end of the needle. Consequently, there is a substantial risk to the person attempting to do this, particularly if the reshielding is attempted during emergency periods or other times of high stress.

Other methods of needle shielding are known and are described, for example, in Bastien U.S. Pat. No. 2,571,653, Leeson et al U.S. Pat. No. 3,890,971 and Wulff U.S. Pat. No. 3,780,734. However, each of these devices suffers from various drawbacks. For example, the Bastien guarded syringe does not positively retain the guard in position, and the devices shown in the Leeson and Wulff patents are quite complex with the latter device being particularly adapted for animal usage.

SUMMARY OF THE INVENTION

This invention provides a hypodermic syringe of simple construction which includes an easily operable guard which can be positively retained in its guarding position. The guard is moved to an extended or guarding position from behind the needle so that there is no danger that the user will be inadvertently pricked by the potentially contaminated needle.

The needle guard of this invention is adapted to be employed with a hypodermic syringe which comprises a barrel adapted to contain a substance to be injected, a hypodermic needle coupled to the barrel and having a passage extending therethrough and terminating in a point, and means, such as a plunger, for forcing the substance from the barrel through the passage of the needle. To simplify construction, the needle guard is mounted on the barrel between an extended position in which the guard obstructs access to the point of the needle and a retracted position in which the guard does not materially obstruct access to the point of the needle.

Means is provided for releasably locking the guard in the retracted position. The mounting means mounts the guard for movement relative to the barrel along a first path when the guard is in the extended position. Means responsive to movement of the guard along the first path when the guard is in the extended position locks the guard in the extended position so that the needle remains shielded. Preferably, the mounting means also mounts the guard for movement along a second path when the guard is in the retracted position, and a releasable locking means is responsive to movement of the guard along the second path to release the guard for travel to the extended position.

The guard is preferably moved axially of the barrel in moving from the retracted position to the extended position. Similarly, both of the first and second paths preferably provide for some circumferential movement of the guard relative to the barrel. Movement of the guard along the first and second paths can advantageously be controlled by a track on at least one of the guard and the barrel and track-engaging means carried by the other of the guard and the barrel.

In a preferred construction, the guard has an internal sleeve with proximal and distal edges, and the track is provided on the sleeve. The track includes first and second track sections opening at the proximal and distal edges, respectively. The sleeve may be a separate element or it may be integral with the guard. The track-engaging means preferably includes first and second track-engaging members cooperating with the first and second track sections, respectively.

The track sections and the associated track-engaging members guide the movement of the guard along the first and second paths. In addition, the locking means for retaining the guard in its two positions can advantageously include a restriction in each of the first and second track sections which impedes movement of the track-engaging member therethrough thereby tending to retain the guard in position.

In a preferred construction, the track-engaging members are axially offset, and each of the first and second track sections includes an axial portion and a circumferentially extending portion, with the axial portions opening at the proximal and distal edges, respectively. The axes of these openings are preferably axially aligned.

To facilitate mounting of the guard on the barrel, the track preferably extends completely through the sleeve from the distal edge to the proximal edge. For example, the track may extend helically. Of course, the track and track-engaging means can be reversed in that the former may be carried by the barrel and the latter by the guard.

The invention, together with additional features and advantages thereof, may best be understood by reference to the following description taken in conjunction with the accompanying illustrative drawing.

BRIEF DESCRIPTION OF THE DRAWING

FIG. 1 is an elevational view of a hypodermic syringe constructed in accordance with the teachings of this invention with the guard being in the extended position and the conventional shield removed.

FIG. 2 is an elevational view similar to FIG. 1 with the guard in the retracted position.

FIG. 3 is a perspective view of the hypodermic syringe with the guard, except for the sleeve portion thereof, being illustrated in dashed lines.

FIG. 4 is a fragmentary sectional view illustrating a portion of the syringe.

DESCRIPTION OF THE PREFERRED EMBODIMENT

FIGS. 1 and 2 show a hypodermic syringe 11 which generally comprises a barrel 13 adapted to contain a substance to be injected, a hypodermic needle 15 having an axial passage extending therethrough, a plunger 17 and a guide 19. The plunger 17 is mounted for axial sliding movement within the barrel for forcing the substance from the barrel through the passage of the needle and a guard 19.

The barrel 13, the needle 15 and the plunger 17 may be of conventional construction. Thus, the barrel 13, the needle 15 and the plunger 17 may be of conventional construction. Thus, the barrel 13 is in the form of a hollow plastic cylinder having appropriate graduations or indicia 21 so that the amount of the substance to be injected can be determined. The barrel 13 has an end wall 23 to which the needle 15 is attached in a conventional manner by a needle mounting member 24. The needle 15 is coaxial with the barrel 13 and terminates in a sharp point 25 at the distal end of the needle. The plunger 17 has a flat outer end 27 which facilitates manual movement of the plunger 17 within the barrel 13 and it may have a piston or other suitable means (not shown) at its inner end to facilitate explusion of the substance from the barrel and through the passage of the needle 15. The syringe 11 may also include a conventional shield 20 in the form of an elongated hollow cylinder which is frictionally retained on the needle mounting member 24.

The guard 19 includes a guard tube 31 and an inner sleeve 33 which may be integral with the tube 31 or a separate member suitably mounted within the tube 31. The tube 31 and the sleeve 33 are preferably constructed from a relatively rigid plastic material. The tube 31 has a cylindrical peripheral wall 35, an open proximal end 37 for receiving the barrel 13 and an annular flange 39 at its distal end defining an opening 41 which is large enough to permit the shield 29 to pass through it. Of course, if the shield 29 is not used, then the opening 41 need only be large enough to allow the needle mounting member 24 to pass through it. The opening 41 could be closed by a material which could be ruptured by the needle 15 and/or the shield 29.

As shown in FIG. 4, the sleeve 33 is much shorter axially than the tube 31, and the tube is spaced radially outwardly slightly from the barrel 13 at locations axially outwardly of the sleeve.

The sleeve 33 has a track 43 which cooperates with track-engaging members 45 and 47. Although the track 43 can be of different configurations, in the embodiment illustrated, it includes a first track section 49 and a second track section 51 opening at a proximal edge 53 and a distal edge 55, respectively, of the sleeve 33. In addition, the track 43 also includes a helical track section 57 extending between the edges 53 and 55. Each of the track sections 49 and 51 includes an axial portion 59 and a circumferentially extending portion 61 with each of the circumferentially extending portions including a restriction 63 which reduces the width of the associated circumferential portion to less than the width of the associated track-engaging members 45 and 47. The axial portions 59 open at the edges 53 and 55, respectively, and the axes of these openings are axially aligned. The track sections 51 and 57 are sized to receive the track engaging member 45 and the track section 49 is sized to receive the track-engaging member 47.

Although the track-engaging members 45 and 47 can be of different constructions, in the embodiment illustrated, each of them is in the form of a short, radially extending pin suitably mounted on the peripheral wall of the barrel 13 and projecting radially outwardly. The members 45 and 47 are axially aligned. If desired, each of the members 45 and 47 may be in the form of a hollow, deformable dimple.

The guard 19 can be assembled onto the barrel 13 by inserting the needle 15 with the shield 29 thereon through the open proximal end 37 and moving the member 45 through the helical track section 57 to the position shown in FIG. 1. Alternatively, the guard may be in the position shown in FIG. 2 for transport and storage in which the member 47 is received within the circumferential portion 61. In this event, the conventional shield 29 would form the only needle protection means prior to use of the needle. In any event, the track section 57 is provided for the purpose of assembling the guard 19 onto the barrel 13 and its helical configuration is optional. The needle 15 can be shipped separately from the syringe, if desired.

Assuming that the syringe 11 is shipped for use with the guard 19 retracted as shown in FIG. 2, then following use of the syringe for injection purposes, the user simply rotates the guard 19 to bring the member 47 into alignment with the axial portion 59, slides the guard 19 axially downwardly to bring the member 45 within the axial portion 59 of the track section 51 and then rotates the guard 19 relative to the barrel to move the member 45 into the circumferential portion 61. By forcing the member 45 through the restriction 63, the guard is tightly retained in the extended position of FIG. 1 following its use. In the extended position, the peripheral wall 35 extends beyond the point 25 of the needle 15 so that the point of the needle is shielded from contact with anyone handling the syringe 11.

The ease with which the members 45 and 47 can move through the respective restrictions 63 can be varied depending upon the results desired. For example, if the syringe 11 is to be shipped in the condition shown in FIG. 1, then it would be desirable to have the member 45 move through the associated restriction 63 with sufficient ease so that use of the syringe is not difficult. On the other hand, if the syringe is to be shipped with the guard 19 in the retracted position of FIG. 2, then the lock provided by the track section 49 and the member 47 must be relatively easily releasable, but the lock provided by the member 45 and the track section 51 can be made so that it is very difficult or impossible to unlock. In any event, to move the guard 19 from the extended position of FIG. 1 to the retracted position of FIG. 2, sequential compound movements are required, and this fact alone makes exposure of a contaminated needle unlikely.

Although an exemplary embodiment of the invention has been shown and described, many changes, modifications and substitutions may be made by one having ordinary skill in the art without necessarily departing from the spirit and scope of this invention.

We claim:

1. A hypodermic syringe comprising:
   a barrel adapted to contain a substance to be injected;
   means for mounting a hypodermic needle to the barrel with the needle having a passage extending therethrough and terminating in a point;
   means for forcing the substance from the barrel through the passage of the needle;
   a needle guard;
   means for mounting the guard on the barrel for movement relative to said barrel, said mounting means mounting the guard for movement between an extended position in which the guard obstructs access to the point of the needle and a retracted position in which the guard does not materially obstruct access to the point of the needle, said extended and retracted positions being axially spaced;

said mounting means mounting said guard for movement relative to the barrel along first and second paths when the guard is in the retracted and extended positions, respectively, said first and second paths including first and second generally circumferentially extending regions, respectively;

first means responsive to movement of said guard along said first path when the guard is in the retracted position for releasably locking the guard in the retracted position;

second means responsive to movement of the guard along the second path when the guard is in the extended position to positively lock the guard in the extended position so that the guard cannot be moved to the retracted position in response to axial force on the guard;

said mounting means including a track carried by at least one of said guard and said barrel and track-engaging means carried by the other of said guard and said barrel for defining said first and second paths;

said guard having an internal sleeve with distal and proximal edges and said track is provided on said sleeve, said track including at least first and second track sections opening at the distal and proximal edges, respectively; and said track-engaging means including first and second track-engaging members mounted on said barrel and adapted to be received in said first and second track sections, respectively.

2. A syringe as defined in claim 1 wherein said sleeve is integral with said guard.

3. A syringe as defined in claim 1 wherein said means for locking the guard in the extended position includes the second track section and the second track-engaging member.

4. A syringe as defined in claim 1 including track means which extends between the proximal and distal edges of the internal sleeve to facilitate mounting of the guard on the barrel.

5. A syringe as defined in claim 1 wherein said first and second track-engaging members are axially offset on said barrel, each of said first and second track sections have an axial portion and a circumferentially extending portion, the axial portions open at the proximal and distal edges, respectively.

6. A syringe as defined in claim 5 wherein the circumferentially extending portions of said first and second tracks extend in the same direction from their respective axially extending portions.

7. An apparatus for injecting a substance into a human or animal comprising:

a body adapted to have the substance to be injected pass therethrough;

means for mounting a needle on the body with the needle having a passage extending therethrough and terminating in a point whereby the substance can pass from the body to and through the passage of the needle;

a needle guard;

means for mounting the guard on the body for movement relative to said body, said mounting means mounting the guard for movement between an extended position in which the guard obstructs access to the point of the needle and a retracted position in which the guard does not materially obstruct access to the point of the needle, said extended and retracted positions being axially spaced;

said mounting means mounting said guard for movement relative to the body along first and second paths when the guard is in the retracted and extended positions, respectively, said first and second paths including first and second generally circumferentially extending regions, respectively;

first means responsive to movement of said guard along said first path when the guard is in the retracted position for releasably locking the guard in the retracted position;

second means responsive to movement of the guard along the second path when the guard is in the extended position to positively lock the guard in the extended position so that the guard cannot be moved to the retracted position in response to axial force on the guard;

said mounting means including means defining a track and track-engaging means cooperable with the track for defining said first and second paths; and said track being on said guard and said track including at least first and second track sections for use in defining said first and second paths and opening at axially spaced locations along the guard.

8. An appartus as defined in claim 7 wherein said track-engaging means includes first and second track-engaging members carried by said body and adapted to be received in said first and second track sections, respectively.

9. An apparatus as defined in claim 8 wherein the means for locking the guard in the extended position includes the second track section and the second track-engaging member.

10. An apparatus as defined in claim 8 wherein said first and second track-engaging members are axially offset, each of said first and second track sections have an axial portion and a circumferentially extending portion with the axial portions opening at said axially spaced locations, said circumferentially extending portions of said first and second track sections cooperating with the first and second track engaging members, respectively, to define said first and second generally circumferential regions, respectively, said first means includes said first track engaging member and said first track section and said second means includes said second track engaging member and said second track section, said first means locking the guard in the retracted position in response to movement of the guard in one direction along said first path and releasing the guard for movement to the extended position in response to movement of the guard in the opposite direction along said first path, said second means being responsive to movement of the guard in a first direction along the second path to lock the guard in the extended position.

11. An apparatus as defined in claim 10 wherein the circumferentially extending portions of said first and second tracks extend in the same direction from their respective axially extending portions.

12. An apparatus as defined in claim 10 wherein said axial portions are in general alignment with each other and said axial portion of said second track section is displaced circumferentially from said second track engaging member when the guard is locked by said first means in said retracted position.

13. An apparatus as defined in claim 11 wherein the first means is responsive to movement of the guard in one direction along the first path to lock the guard in the retracted position and is responsive to movement of the guard in the opposite direction along the first path to release the guard for movement to the extended position.

* * * * *